US010111678B2

(12) United States Patent
Jinno et al.

(10) Patent No.: US 10,111,678 B2
(45) Date of Patent: Oct. 30, 2018

(54) MEDICAL MANIPULATOR AND METHOD OF CONTROLLING THE SAME

(71) Applicant: MEDICAROID CORPORATION, Chuo-ku, Kobe-shi, Hyogo (JP)

(72) Inventors: Makoto Jinno, Tokyo (JP); Hiroaki Sano, Yamanashi (JP)

(73) Assignee: MEDICAROID CORPORATION, Kobe-Shi, Hyogo (JP)

(*) Notice: Subject to any disclaimer, the term of this patent is extended or adjusted under 35 U.S.C. 154(b) by 83 days.

(21) Appl. No.: 14/964,696

(22) Filed: Dec. 10, 2015

(65) Prior Publication Data
US 2016/0100898 A1 Apr. 14, 2016

Related U.S. Application Data

(63) Continuation of application No. PCT/JP2013/003702, filed on Jun. 13, 2013.

(51) Int. Cl.
*G06F 19/00* (2018.01)
*A61B 17/29* (2006.01)
(Continued)

(52) U.S. Cl.
CPC .......... *A61B 17/29* (2013.01); *A61B 19/2203* (2013.01); *A61B 34/30* (2016.02); *A61B 34/37* (2016.02); *A61B 2017/2902* (2013.01)

(58) Field of Classification Search
CPC ......... A61B 17/29; A61B 34/30; A61B 34/37; A61B 16/2203; A61B 2017/2902;
(Continued)

(56) References Cited

U.S. PATENT DOCUMENTS 8,010,180 B2 * 8/2011 Quaid ........................... 600/424
8,623,030 B2 * 1/2014 Bonutti .............. A61B 19/2203
606/130

(Continued)

FOREIGN PATENT DOCUMENTS

| JP | 2005-34991 A | 2/2005 |
| JP | WO 2006/079108 A1 | 7/2006 |
| JP | 2008-526130 A | 7/2008 |

OTHER PUBLICATIONS

International Search Report (PCT/ISA/210) dated Jul. 16, 2013, by the Japanese Patent Office as the International Searching Authority for International Application No. PCT/JP2013/003702.

*Primary Examiner* — Ronnie M Mancho
(74) *Attorney, Agent, or Firm* — Buchanan Ingersoll & Rooney PC

(57) ABSTRACT

A medical manipulator is disclosed, which includes a multiple-degree freedom arm which can be mounted with a medical instrument, an insertion port position which indicates a spatial position of an insertion port for inserting the medical instrument mounted in the multiple-degree freedom arm into a human body is retained, and the multiple-degree freedom arm is controlled so as to insert the medical instrument into the human body from the retained insertion port position. The multiple-degree freedom arm is driven under operational restriction in which movement of the medical instrument is restricted by the insertion port position after the medical instrument is inserted from the insertion port position. The multiple-degree freedom arm is driven so as to move a predetermined portion of the medical instrument to spatial coordinates instructed by a user while maintaining a state where the medical instrument passes through the insertion port position under the operational restriction.

20 Claims, 11 Drawing Sheets

(51) Int. Cl.
*A61B 19/00* (2006.01)
*A61B 34/30* (2016.01)
*A61B 34/37* (2016.01)

(58) Field of Classification Search
CPC ............... A61B 90/06; A61B 18/1492; A61B 2034/301; A61B 2090/061; A61B 2090/065
USPC .......................................................... 700/245
See application file for complete search history.

(56) References Cited

U.S. PATENT DOCUMENTS

| | | | | |
|---|---|---|---|---|
| 2002/0082612 A1* | 6/2002 | Moll | ................. | A61B 19/2203 606/130 |
| 2002/0128552 A1* | 9/2002 | Nowlin | ................. | A61B 34/70 600/427 |
| 2006/0167440 A1 | 7/2006 | Cooper et al. | | |
| 2006/0276686 A1* | 12/2006 | Tsuji | ........................ | A61B 5/06 600/117 |
| 2010/0174410 A1* | 7/2010 | Greer | ..................... | B25J 9/1671 700/264 |
| 2010/0234857 A1* | 9/2010 | Itkowitz | ............... | G09B 23/285 606/130 |
| 2011/0319815 A1* | 12/2011 | Roelle | ................. | A61B 1/00149 604/95.01 |
| 2013/0024024 A1* | 1/2013 | Namiki | .............. | A61B 1/00149 700/245 |
| 2013/0072784 A1* | 3/2013 | Velusamy | .......... | A61B 17/3403 600/424 |
| 2013/0303892 A1* | 11/2013 | Zhao | ..................... | A61B 5/061 600/424 |
| 2013/0345718 A1* | 12/2013 | Crawford | ............. | A61B 17/025 606/130 |
| 2016/0100898 A1* | 4/2016 | Jinno | .................... | A61B 34/30 606/130 |
| 2016/0100899 A1* | 4/2016 | Jinno | .................... | A61B 34/30 606/130 |

* cited by examiner

MEDICAL MANIPULATOR AND METHOD OF CONTROLLING THE SAME

CROSS-REFERENCE TO RELATED APPLICATIONS

This application is a continuation of International Application No. PCT/JP2013/003702 filed on Jun. 13, 2013, the entire content of which is incorporated herein by reference.

TECHNICAL FIELD

The present disclosure relates to a medical manipulator and a method of controlling the same in a remote operation-type surgery system, and particularly relates to a medical manipulator and a method of controlling the same suitable to support minimally invasive surgery such as laparoscopic surgery and laparo-thoracoscopic surgery, which are conducted by inserting a medical instrument such as an endoscope and forceps into a human body.

BACKGROUND DISCUSSION

A minimally invasive surgical operation can have numerous advantages compared to traditional technology of laparotomy, for example, there can be less postoperative pain, a hospital stay can be lessened, returning to normal activities (re-integration into society) can be quickened, and there can be less damage to tissues. Meanwhile, a surgeon can be required to have high-level techniques and considerable expertise due to constraints such as operations, a field of vision, and surgical instruments. As a result, there is a strong and growing need for the minimally invasive surgical operation in which a robot surgical operation system capable of avoiding such constraints can be applied.

Laparoscopic surgery is a type of a minimally invasive surgical operation. In the laparoscopic surgery, a laparoscope and forceps are inserted into an abdominal cavity through a small incision site on an abdominal wall of a patient through the abdominal wall. An operator conducts surgery using the forceps while observing tissues of the abdominal cavity through the laparoscope. Generally, an abdominal cavity is expanded by using carbon dioxide. In order to realize the above-described procedure, an instrument, that is, a so-called trocar is inserted through the incision site on the abdominal wall, and the laparoscope and the forceps are inserted into an abdominal cavity via the trocar. In this manner, most of the surgical operation procedure can be conducted without requiring incision for a large or open cavity in a surgical operation.

JP-T-2008-528130 discloses a remote operation-type surgery system that can be in operation by performing remote-operation of the forceps, which is inserted into an abdominal cavity and carries out treatment, thereby allowing the above-described laparoscopic surgical operation to be relatively easily and safely conducted.

SUMMARY

However, in the above-described remote operation-type surgery system including a plurality of arms, measures to cope with variations of a trocar position have not been taken into consideration. When the trocar position varies, there can be a need to change the mechanical setting and physical disposition of the arms in accordance therewith, which can result in a lack of convenience.

A remote operation-type surgery system is disclosed, which can flexibly cope with variations of an insertion port position during surgery which is conducted by causing a medical instrument such as forceps used in laparoscopic surgery to be inserted into a human body from an insertion port.

In accordance with an exemplary embodiment, a medical manipulator is disclosed, which can include a multiple-degree freedom arm, which can be mounted with a medical instrument. The medical manipulator can include retention means for retaining an insertion port position which indicates a spatial position of an insertion port for inserting the medical instrument mounted in the multiple-degree freedom arm into a human body, insertion control means for controlling the multiple-degree freedom arm so as to insert the medical instrument into the human body from the insertion port position, and drive control means for driving the multiple-degree freedom arm under operational restriction in which movement of the medical instrument is restricted by the insertion port position after the medical instrument is inserted from the insertion port position by using the insertion control means.

The drive control means can drive the multiple-degree freedom arm so as to move a predetermined portion of the medical instrument to spatial coordinates instructed by a user while maintaining a state where the medical instrument passes through the insertion port position under the operational restriction.

In accordance with an exemplary embodiment, a method is disclosed of controlling a medical manipulator including a multiple-degree freedom arm, which can be mounted with a medical instrument, the method comprising: retaining an insertion port position which indicates a spatial position of an insertion port for inserting the medical instrument mounted in the multiple-degree freedom arm into a human body, in a memory; controlling the multiple-degree freedom arm so as to insert the medical instrument into the human body from the insertion port position; driving the multiple-degree freedom arm under operational restriction in which movement of the medical instrument is restricted by the insertion port position after the medical instrument is inserted from the insertion port position; and driving the multiple-degree freedom arm so as to move a predetermined portion of the medical instrument to spatial coordinates instructed by a user while maintaining a state where the medical instrument passes through the insertion port position under the operational restriction.

According to the present disclosure, a remote operation-type surgery system can be provided, which can flexibly cope with variations of an insertion port position for a medical instrument such as forceps and the like with respect to a human body, for example.

Other characteristics and advantages of the present disclosure will be clear in the following descriptions with reference to the accompanying drawings. Note that, the same reference numerals and signs will be applied to the same or similar configurations in the accompanying drawings.

BRIEF DESCRIPTION OF THE DRAWINGS

Description includes the accompanying drawings, which are configured to be a part thereof, illustrate exemplary embodiments of the present disclosure, and are applied to explain principles of the present disclosure together with the description thereof.

DETAILED DESCRIPTION

Hereinafter, an example according to an exemplary embodiment of the present disclosure will be described with reference to the accompanying drawings.

Figure 1:
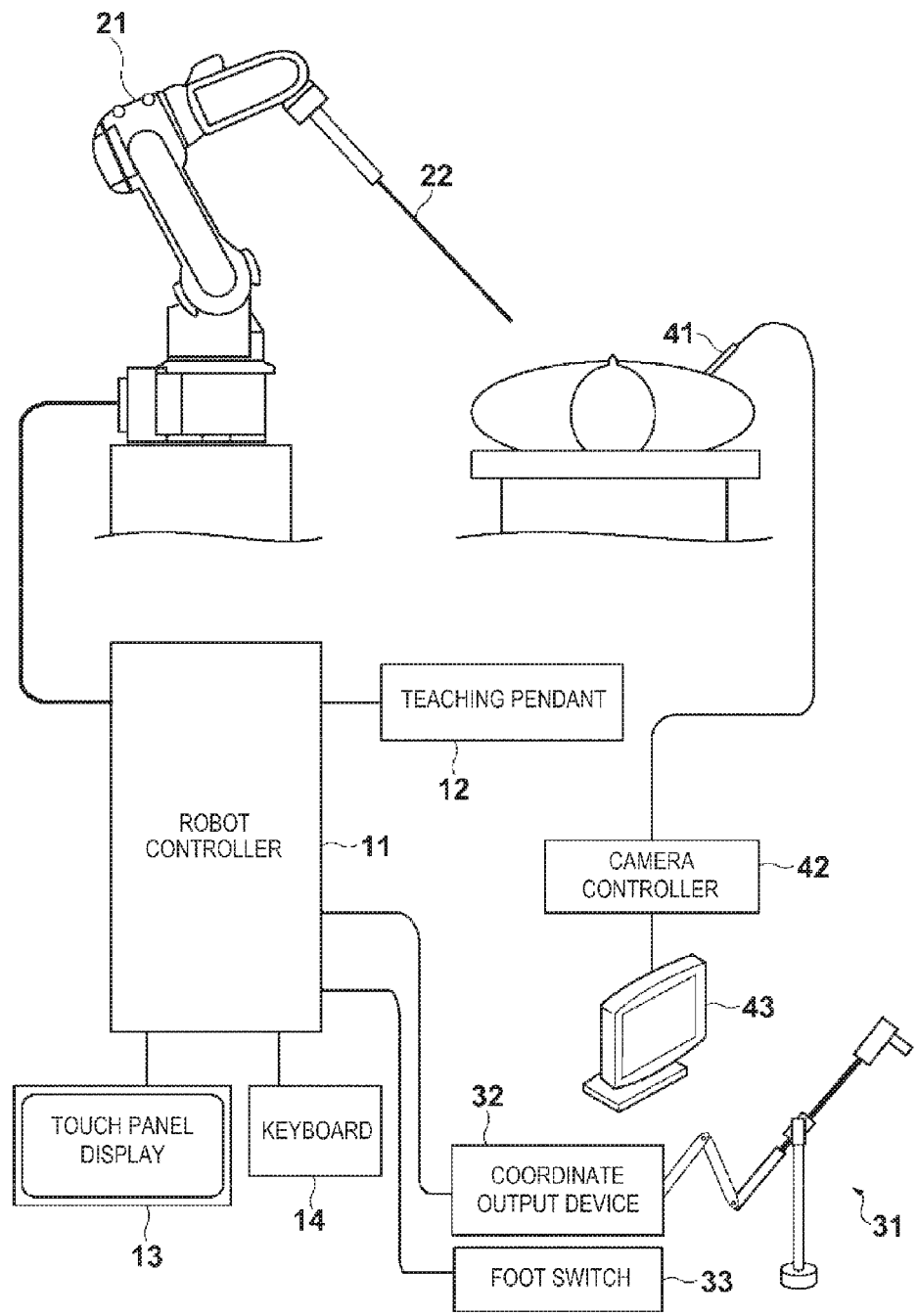
FIG. 1 is a diagram illustrating a configuration of a remote operation-type surgery system in accordance with an exemplary embodiment.

FIG. 1 is a diagram illustrating an example of a remote operation-type surgery system in the embodiment. In the configuration illustrated in FIG. 1, a slave arm 21 which is a multiple-degree freedom robot arm operates following after movement of a master arm 31. As an operator operates the master arm 31, minimally invasive surgery such as laparoscopic surgery can be realized by performing remote operation.

In accordance with an exemplary embodiment, a robot controller 11 controls driving of each of axes of the slave arm 21. Operation interfaces such as a teaching pendant 12, a touch panel display 13, and a keyboard 14 can be connected to the robot controller 11, as necessary. The teaching pendant 12 instructs the robot controller 11 to perform a jog operation of the slave arm 21 in accordance with a user's operation. The touch panel display 13 displays various operation states of the slave arm 21 and provides a graphical user interface for performing various operational instructions. The keyboard 14 is applied to input various items of data into the robot controller 11. For example, a user applies the keyboard 14 so as to be able to input a coordinate value of a teaching position for the slave arm 21 and to make an instruction for the jog operation. Note that, in accordance with an exemplary embodiment, the jog operation denotes an operation in which a robot is guided at a predetermined speed in a predetermined direction or the robot in a predetermined axis is driven at a predetermined speed through the operation interfaces such as the teaching pendant 12, the touch panel display 13, and the keyboard 14 by performing an ON/OFF operation or the like with buttons.

As the slave arm 21, for example, a six-axis vertical articulated robot arm can be applied, and which is generally used as an industrial robot. Forceps 22 for conducting the laparoscopic surgery can be mounted at a distal end portion of the slave arm 21. Note that, the degree of freedom of the slave arm 21 is not limited to six axes, and disposition of the degree of freedom is not limited as well. However, there is a need to have the degree of freedom to the extent in which operations required in the laparoscopic surgery can be realized, and disposition of the degree of freedom. The slave arm 21 will be described later in detail with reference to FIGS. 2A and 2B.

The forceps which have been mounted in a surgery robot can be multiple-degree freedom forceps, which include yaw axis-roll axis or pitch axis-yaw axis-gripper axis for the distal end portion. A gripper can be guided to be positioned in arbitrary position and posture inside an abdominal cavity. However, the surgery robot is not necessarily to be the multiple-degree freedom forceps. Therefore, in this disclosure, detailed descriptions will not be particularly given regarding the degree of freedom of the distal end portion of the forceps. Meanwhile, when exhibiting surgical techniques, it can be natural that end effectors in any form such as a gripper, scissors, an L-shaped hook, an electrical scalpel, and an energy device are necessary regardless of the presence or absence of an articulation of the distal end portion or the degree of freedom of the end effectors. In addition, it is possible to have a configuration as an endoscope retention arm by causing the arm to retain an endoscope (an endoscope such as a laparoscope, a thoracoscope, a hysteroscope, and a nasoscope, with which the inside of a human body can be observed).

The master arm 31 can provide an operation unit with which an operator instructs the slave arm 21 to make a movement of the forceps 22. A coordinate output device 32 outputs a spatial position instructed through the master arm 31 to the robot controller 11 as a three-dimensional coordinate value. Note that, the coordinate output device 32 may have been built in the robot controller 11. The configuration of the master arm 31 and the coordinate value output by the coordinate output device 32 will be described later in detail with reference to FIG. 3. A foot switch 33 outputs an in-operation signal to the robot controller 11. The in-operation signal indicates a state of effectiveness or ineffectiveness of an operation performed by the master arm 31. Note that, the configuration for generating such an in-operation signal is not limited to the foot switch. For example, it is acceptable as long as an in-operation signal is output in accordance with a user's operation other than the user's operation for designating the spatial position of the forceps 22. For example, a holding portion of the master arm 31 may be provided with an ON-OFF switch for the in-operation signal.

A camera 41 images the inside of an abdominal cavity of a patient and transmits an image signal thereof to a camera controller 42. The camera controller 42 causes a monitor 43 to display the image signal received from the camera 41. An operator can conduct surgery by operating the master arm 31 while checking a position of the forceps 22 inside the abdominal cavity moved by the slave arm 21, positions of internal organs (target lesion) of a patient, and the like through the monitor 43. Accordingly, the operator can conduct surgery under an environment similar to that of general laparoscopic surgery.

Figure 2:
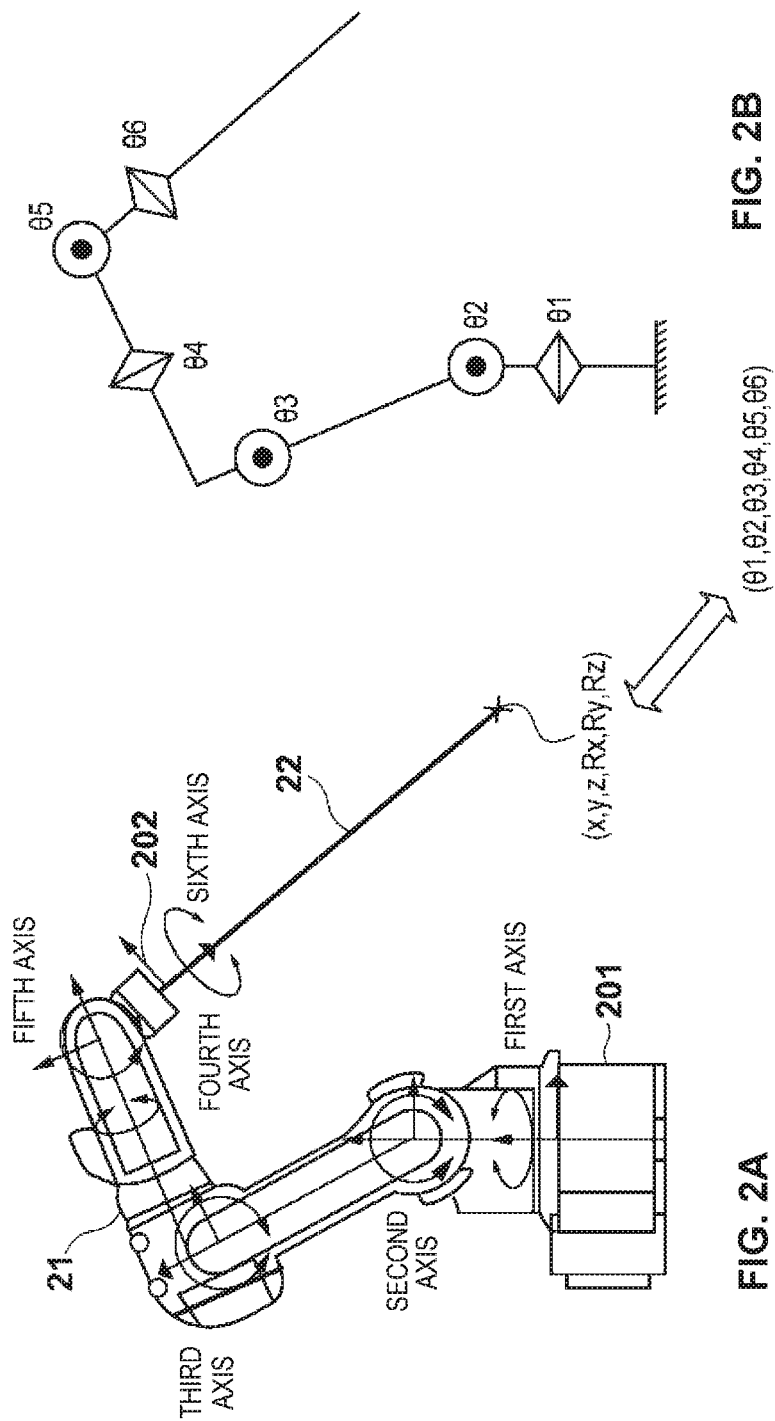
FIGS. 2A and 2B are diagrams illustrating a slave arm in accordance with an exemplary embodiment.

FIGS. 2A and 2B are diagrams illustrating the slave arm 21 in the present exemplary embodiment. As described above, the slave arm 21 is a six-axis articulated arm, which can include a first axis, a second axis, and so forth to a sixth axis in order from the side of a base 201, as illustrated in FIG. 2A. For example, each of the axes is rotatively driven by a servo motor. FIG. 2B schematically shows each of the axes and the arm of the slave arm 21. The reference numerals and signs θ1 to θ6 respectively indicate rotary angles (positions) around each of the axes from the first axis to the sixth axis.

A position of the distal end portion of the forceps 22 is represented by three-dimensional coordinates (x, y, and z), and a posture of the forceps 22 is represented by angles (Rx, Ry, and Rz) around the axes x, y, and z, for example. The position and the posture of the forceps 22 are uniquely determined to be the factors (x, y, z, Rx, Ry, and Rz), and each of the angles (θ1, θ2, θ3, θ4, θ5, and θ6) of the axes from the first axis to the sixth axis for realizing the position and the posture thereof is calculated by inverse kinematics computation. In addition, the position and the posture (x, y, z, Rx, Ry, and Rz) of the forceps 22 can be obtained by forward kinematics computation based on each of the angles (θ1, θ2, θ3, θ4, θ5, and θ6) of the axes from the first axis to the sixth axis.

A forceps mounting portion 202 is provided at the distal end portion of the slave arm 21, and the forceps 22 are mounted therein. The forceps 22 can be configured to be suitably replaced in accordance with techniques by being configured to be attachable and detachable with respect to the forceps mounting portion 202. Here, if the sixth axis (a rotary axis) is caused to coincide with a shaft of the forceps 22 (a forceps shaft), that is, a major axis of the forceps 22, a rotative operation of the forceps shaft can be realized by driving only the sixth axis, thereby being convenient. In accordance with an exemplary embodiment, for example, the forceps shaft can rotate without moving the first axis to the fifth axis, and the arm does not move in its entirety when the forceps shaft rotates. Therefore, a risk of interference with other arms can be reduced when multiple slave arms are installed, and thus, a drive range of the articulation can be moderated or an operation speed of the articulation can be limited. In addition, positioning of an end effector can be performed at the distal end portion of the forceps inside an abdominal cavity of a patient and the end effector can be rotated around the forceps shaft by providing the end effector such as a gripper axis and the like at the distal end portion of the forceps, and thus, general techniques related to the laparoscope can be realized.

Figure 3:
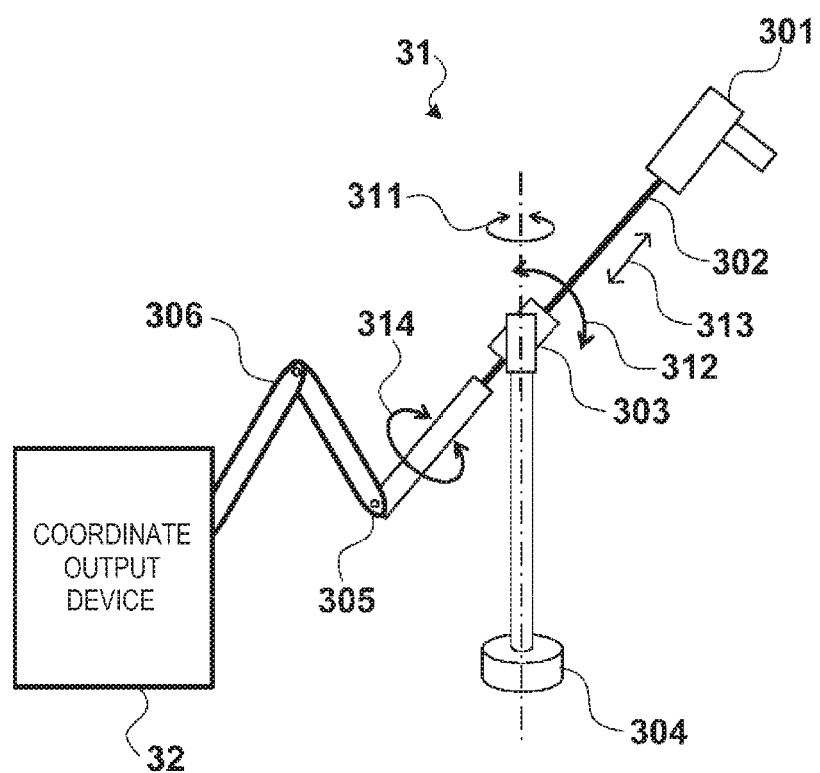
FIG. 3 is a diagram illustrating a master arm in accordance with an exemplary embodiment.

FIG. 3 is a diagram illustrating the master arm 31 in accordance with an exemplary embodiment. The master arm 31 can include a master forceps handle 301, a master forceps shaft 302, a virtual trocar portion 303, a base 304, and a position transmission mechanism 306. The master forceps handle 301 is a portion to be held by an operator to operate the master forceps shaft 302. When the forceps 22 includes a drive unit for driving the gripper, or an articulation axis or the like at the distal end portion of the forceps, a user interface for operating the drive unit thereof may be provided in the master forceps handle 301.

The master forceps shaft 302 can be supported in two axes by the virtual trocar portion 303 so as to be rotatable with respect to the base 304 and is supported so as to be cylindrically slidable. On account of the two-axis rotative support, the master forceps shaft 302 is supported so as to be able to perform a rotation 311 around the vertical axis and a rotation 312 around the horizontal axis. In addition, on account of the cylindrical sliding support, the master forceps shaft 302 is supported so as to be able to perform sliding in a shaft axis direction 313 and a rotation 314 of the shaft.

According to the above-described configuration, an operator can move a distal end portion 305 of the master forceps shaft 302 to an arbitrary position in a three-dimensional space. When the position transmission mechanism 306 has a configuration similar to that of the six-axis vertical articulated robot arm, the position of the distal end portion 305 in a three-dimensional space (the spatial position) is transmitted to the coordinate output device 32 via the position transmission mechanism 306, and thus, the coordinate output device 32 can output the coordinate values (x, y, and z) corresponding to the three-dimensional position thereof to the robot controller 11. Note that, a rotary angle (r) of the rotation 314 of the shaft is also output to the robot controller 11 via the coordinate output device 32.

In addition, the spatial position of the shaft to be detected is not limited to the distal end portion 305. It is acceptable as long as the spatial position is for a particular portion of the shaft which is operated by a user. However, it can be desirable to provide the virtual trocar portion 303 between a portion (the master forceps handle 301) with which a user holds the master forceps shaft 302 and the particular portion of which the spatial position is detected. In addition, a sensor may be disposed for the two-axis rotative support (the vertical axis and the horizontal axis) of the virtual trocar portion 303 and the cylindrical sliding support (a forceps insertion direction and the rotary axis around the forceps shaft) so as to detect a position of the particular portion of the master forceps shaft 302. According to such a configuration as well, the position of the distal end portion 305 in a three-dimensional space (the spatial position: the coordinate values (x, y, and z) corresponding to the three-dimensional position) and the rotary angle (r) of the rotation 314 of the shaft can be output to the robot controller 11.

In accordance with an exemplary embodiment, an operator holds the master forceps handle 301 and operates the master forceps shaft 302 which is supported by the virtual trocar portion 303 while watching the monitor 43, thereby conducting surgery in which the forceps 22 mounted in the slave arm 21 is applied. In this manner, since the master forceps shaft supported by the virtual trocar portion 303 is operated, surgery conducted through remote operation can be realized with feeling of operation similar to that of operation of forceps performed during conventional laparoscopic surgery. Moreover, the forceps can be operated in an optimal posture and easy to operate the forceps at all times without operating the forceps in a tough posture over a surgical table and without being interfered with an assistant doctor.

Figure 4:
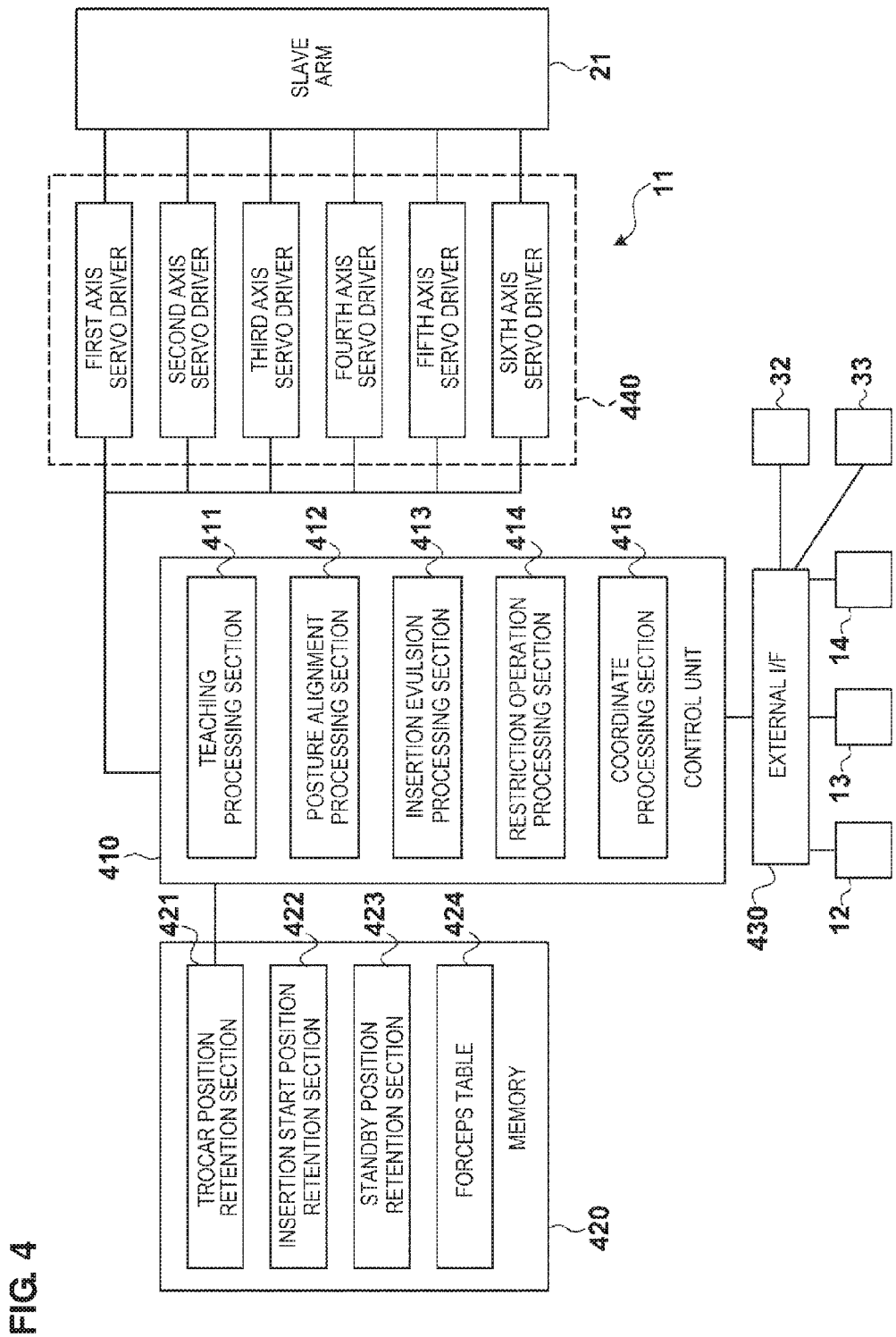
FIG. 4 is a block diagram illustrating a configuration example of a robot controller in accordance with an exemplary embodiment.

FIG. 4 is a block diagram illustrating a configuration example of the robot controller 11. The robot controller 11 can include a control unit 410, a memory 420, an external interface (an external I/F) 430, and a servo driver 440. The control unit 410 can include a CPU, a ROM, a RAM, and the like (not illustrated) and functions as a teaching processing section 411, a posture alignment processing section 412, an insertion evulsion processing section 413, a restriction operation processing section 414, and a coordinate processing section 415 so as to realize each step of the below-described processing. For example, as the CPU executes a program stored in the ROM or the RAM, each of the processing sections can be realized. Operations of each of the processing sections in detail are disclosed through the following descriptions.

For example, the memory 420 is a secondary storage device which is configured to be a hard disk, a semiconductor memory, or the like and can include a trocar position retention section 421, an insertion start position retention section 422, a standby position retention section 423, and a forceps table 424. The trocar position retention section 421 retains coordinates of a position (a trocar position) at which the forceps is inserted into a human body of a patient during laparoscopic surgery, and an insertion posture thereof. The trocar position and the insertion posture are standards for a spatial position (three-dimensional coordinates) of a trocar so as to insert the forceps 22 into an abdominal cavity, and an insertion direction of the forceps 22 into the trocar. In accordance with an exemplary embodiment, a user can designate the trocar position and the insertion posture by performing a teaching operation while being under the control of the teaching processing section 411.

In accordance with an exemplary embodiment, for example, the trocar can be configured to include a forceps insertion portion (an opening portion), and a tubular portion which is inserted through an abdominal wall. However, the trocar position mentioned herein is a position in the vicinity into which the tubular portion has been inserted in the abdominal wall portion, that is, the vicinity of an intersection point between the abdominal wall portion and the tubular portion. The trocar position denotes a position of a fulcrum (a steady point) when the forceps shaft is inserted into an abdominal cavity.

The trocar position retention section 421 can retain the insertion postures corresponding to a plurality of the trocar positions. A desired trocar position can be selected from the plurality of trocar positions as a user performs inputting through the touch panel display 13 or the keyboard 14. The insertion start position retention section 422 retains a starting position and a posture of an insertion operation when the forceps 22 are inserted toward the selected trocar position. The standby position retention section 423 retains a position and a posture of the slave arm 21 in a standby state, and a user can mount and replace the forceps 22 at the position. The types of the forceps, lengths of the forceps shaft, and forceps coordinate systems have been correspondingly recorded in the forceps table 424. The forceps coordinate system can be defined by a standard position of the slave arm, for example, the position and the posture with respect to a mechanical interface.

The servo driver 440 controls driving of the servo motors corresponding to the first axis to the sixth axis of the slave arm 21. The control unit 410 instructs the servo driver 440 of an amount of driving of each of the axes or acquires rotary positions ($\theta 1$ to $\theta 6$) of each of the axes. The teaching pendant 12, the touch panel display 13, the keyboard 14, the coordinate output device 32, and the foot switch 33 are connected to the external I/F 430. In accordance with an exemplary embodiment for example, when the distal end portion of the forceps includes the articulation axis or the gripper axis, a servo driver for driving the articulation axis or the gripper axis at the distal end portion of the forceps may be added inside the servo driver 440.

Figure 5:
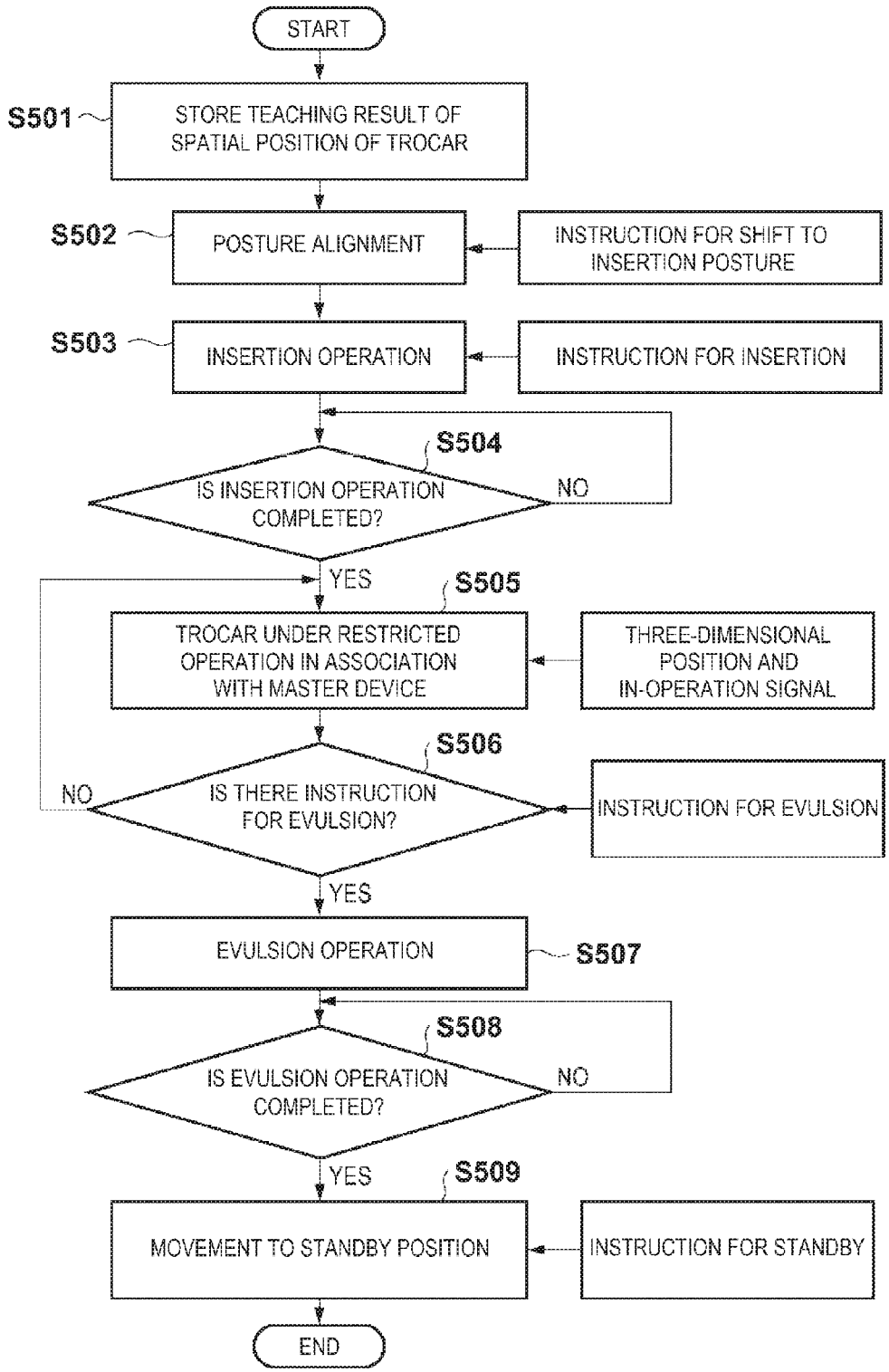
FIG. 5 is a flow chart illustrating a support operation for laparoscopic surgery conducted through remote operation in accordance with an exemplary embodiment.

Subsequently, descriptions will be given regarding an operation of the remote operation-type surgery system in the present embodiment including the above-described configuration. FIG. 5 is a flow chart illustrating an operation of the robot controller 11 in the present exemplary embodiment in a laparoscopic surgery mode.

In the laparoscopic surgery, first, there is a need to cause the robot controller 11 (the trocar position retention section 421) to store the trocar position, which is a forceps insertion position with respect to an abdominal cavity of a patient, and the insertion posture, which is the insertion direction for the forceps through teaching. When a teaching mode is designated through the user interface (hereinafter, referred to as GUI, not illustrated) which is provided by the touch panel display 13, the teaching processing section 411 executes the teaching processing of Step S501. Then, teaching results (vectors indicating the three-dimensional coordinate value and the insertion direction) of the trocar position and the insertion posture are retained in the trocar position retention section 421.

In teaching of the trocar position and the insertion posture, for example, the slave arm 21 is moved by an operation of the teaching pendant 12 or in a manual manner, the distal end portion of the forceps 22 is caused to coincide with the forceps insertion position of a patient, and the insertion posture of the forceps 22 is adjusted. Then, the GUI is operated in the aforementioned state, thereby making an instruction of a determined result. In accordance with the instruction, the teaching processing section 411 calculates the three-dimensional coordinates (x, y, and z) of the distal end portion of the forceps 22 based on the rotary angle ($\theta 1$ to $\theta 6$) of each of the axes and the length of the mounted forceps 22 (the forceps coordinate system) at the moment thereof, and the calculated result is retained in the trocar position retention section 421. In addition, the vectors, for example, (Rx, Ry, and Rz) indicating axial directions of the forceps 22 are calculated, and the calculated result is retained in the trocar position retention section 421 as the insertion posture. Note that, (Rx, Ry, and Rz) indicate the rotary angles around the axes x, y, and z. Note that, a method of teaching the trocar position or the insertion posture is not limited thereto. The three-dimensional coordinates or the insertion posture of the forceps insertion position may be input by using the keyboard 14. In addition, the length of the mounted forceps 22 (the forceps coordinate system) can be acquired from the forceps table 424 in accordance with the type of the forceps 22 input by a user. Note that, acquisition of the length of the forceps 22 is not limited to the above-described method. The length of the mounted forceps 22 may be directly input by using the keyboard 14.

Moreover, in accordance with an exemplary embodiment, the length of the forceps 22 may be acquired through a position and posture measurement system in which three-dimensional position and posture of the trocar can be acquired with respect to a base coordinates system of a robot, or a world coordinate system (the base coordinates system of a robot can be defined with respect to the world coordinate system). In addition, it is acceptable as long as the data to be acquired is basically the three-dimensional position of the trocar. However, as posture information is also acquired, the posture information can be utilized when determining whether or not the forceps insertion direction is appropriate, or the like (will be described later). Thus, a safer system can be established. In addition, even when a position at which a movable area of the slave arm 21 exceeds a permissible range for insertion with respect to each of the trocar positions cannot be taken, there is no need to control the insertion posture with respect to the trocar position.

Subsequently, when an instruction for a shift to the insertion posture is made via the GUI, the posture alignment processing section 412 moves the slave arm 21 to the insertion posture in Step S502. The insertion posture is a posture in which the major axis of the forceps 22 (the forceps shaft) is coincided on a straight line passing through the distal end portion of the forceps 22 and the trocar position. If the posture is included in a predetermined range (the permissible range) having a direction indicated by the insertion posture which has been stored in the trocar position retention section 421 while being correspondingly to the trocar position, as a standard, it is considered that posture alignment with respect to the insertion posture has been completed. As the posture alignment with respect to the insertion posture ends, the forceps 22 move in the major axis direction of the forceps 22 in a parallel manner, and then, the forceps 22 is inserted into an abdominal cavity of a patient from the trocar position. In accordance with an exemplary embodiment, for example, when the direction of the forceps 22 in a result of the posture alignment processing is not included within the permissible range, a user can be notified of such a fact.

In the present exemplary embodiment, the posture alignment processing for the slave arm 21 with respect to the insertion posture can include four modes as described below.

Automatic Mode: The slave arm 21 is moved to the insertion posture in which the distal end portion of the forceps 22 coincides with the three-dimensional position retained in the insertion start position retention section 422 through an articulation synchronous operation or a linear interpolation operation of the first axis to the fifth axis.

Articulation Synchronous Operation Mode: The first to third axes are fixed, and the posture alignment is performed so as to cause the trocar position to match the major axis direction of the forceps 22 through an articulation synchronous operation of the fourth and fifth axes.

Jog Operation Mode: The first to third axes are fixed, and the posture alignment is performed so as to cause the trocar position to match the major axis direction of the forceps 22 through a jog operation of the fourth and fifth axes.

Manual Mode: The first to third axes are fixed, and the posture alignment is performed so as to cause the trocar position to match the major axis direction of the forceps 22 through a manual operation of the fourth and fifth axes.

In accordance with an exemplary embodiment, for example, in the operation modes described above, the sixth axis is not directly engaged with the insertion posture. However, the sixth axis may be included in the modes when a posture of the end effector (a shaft rotary axis) needs to be restricted. In addition, when a forceps distal end articulation axis or the gripper axis is included, the axes need to be guided to an insertable posture (for example, the pitch axis and the yaw axis are in a straight state in the same direction as the shaft, and the gripper is in a closed state) at the same time, before, or after the posture alignment processing. In accordance with an exemplary embodiment, for example, as a method of teaching of the insertion posture for the forceps distal end articulation axis or the gripper axis, the guidance can be considered through the automatic operation, the JOG operation, or the manual operation, similar to the slave arm 21.

In addition, when the forceps shaft rotary axis and the sixth axis do not coincide with each other, since a posture for the posture alignment cannot be uniquely determined with only the fourth and fifth axes, there is a need to make determination including a posture of the forceps shaft rotary axis. In such a case, the automatic mode for the automatic operation performed by the first to sixth axes is applied. In addition, in the articulation synchronous operation mode, the jog operation mode, and the manual mode in which the first to third axes are fixed, when the direction of the forceps 22 is out of the above-described permissible range as a result of the posture alignment processing, a user may be urged to make an instruction of the posture alignment processing to be performed through the automatic mode.

Figure 6A:
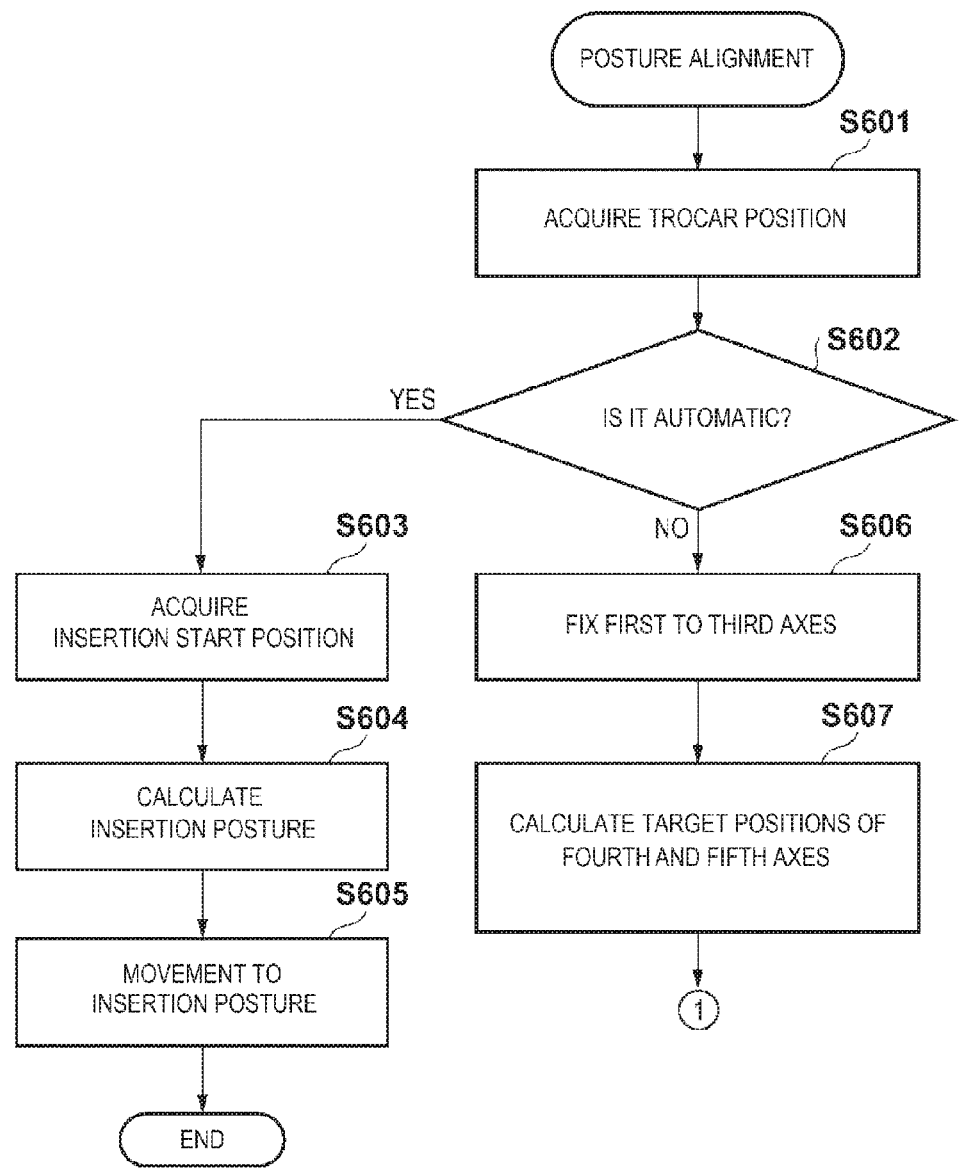
FIG. 6A is a flow chart illustrating a posture alignment operation in accordance with an exemplary embodiment.
Figure 6B:
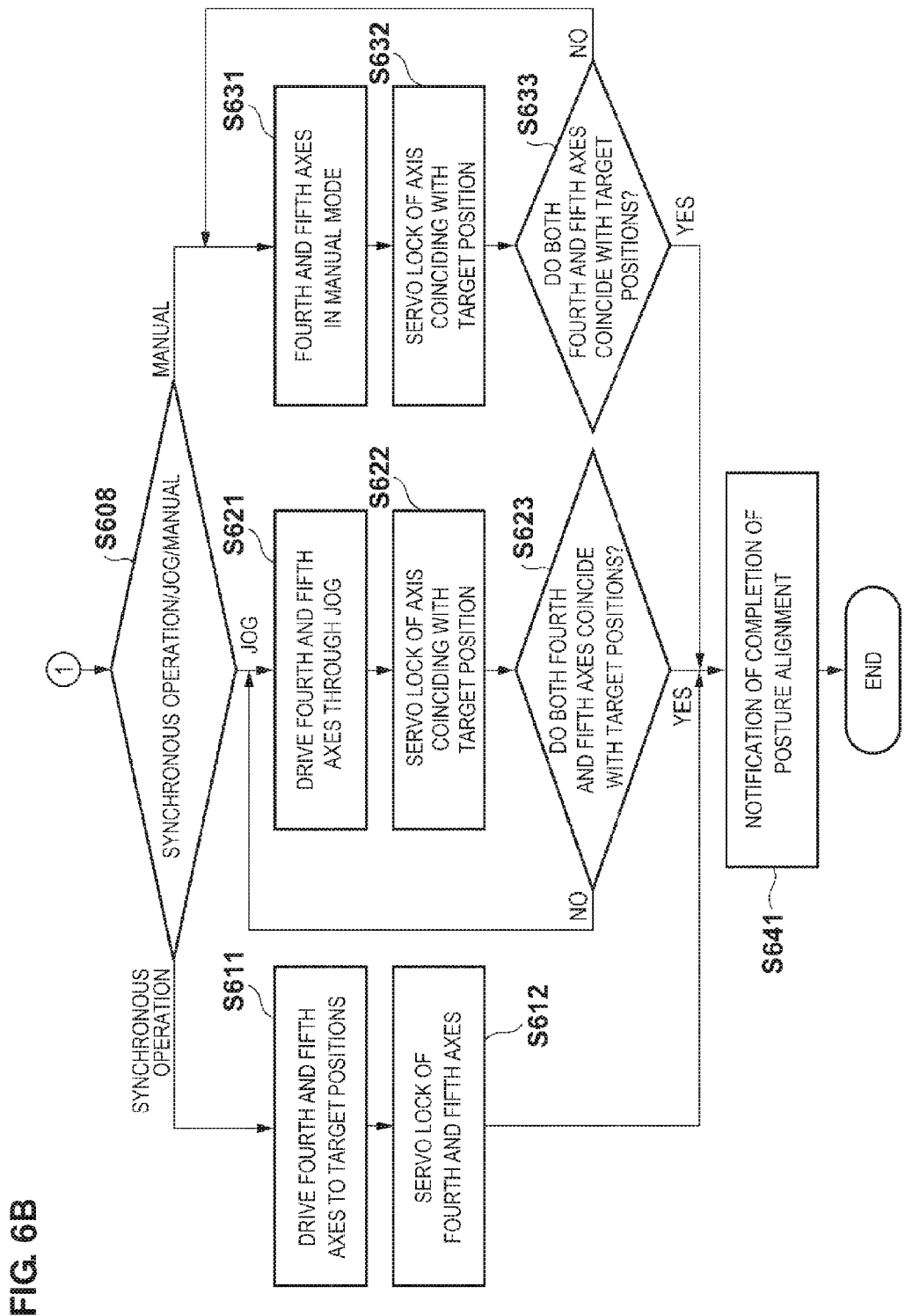
FIG. 6B is a flow chart illustrating another posture alignment operation in accordance with an exemplary embodiment.

Hereinafter, the posture alignment processing according to the present embodiment will be described further with reference to FIGS. 6A and 6B. First, in accordance with an instruction for a shift to the insertion posture, the posture alignment processing section 412 reads out the trocar position from the trocar position retention section 421 (Step S601). When the plurality of trocar positions have been retained in the trocar position retention section 421, a user is caused to select a desired trocar position through the GUI. Otherwise, the trocar position at the time of insertion or evulsion in the previous stage is stored, and the trocar position may be applied as a default position. Hereinafter, the three-dimensional coordinates of the designated trocar position at which the forceps 22 is inserted are referred to as (xt, yt, and zt).

When the automatic mode has been selected, the processing proceeds from Step S602 to Step S603. In Step S603, the posture alignment processing section 412 reads out an insertion start position from the insertion start position retention section 422. When a plurality of the insertion start positions have been retained in the insertion start position retention section 422, a user is caused to select a desired insertion start position through the GUI. Otherwise, the position at the time of insertion or evulsion in the previous stage may be stored so as to be applied as a default position for the insertion start position. Hereinafter, the three-dimensional coordinates of the read out or selected insertion start position are referred to as (xs, ys, and zs). Note that, it can be considered that a position away from the trocar position by, for example, approximately 50 mm to 100 mm along the insertion direction can be automatically calculated and retained in the insertion start position retention section 422. In this case, a user may be allowed to designate a clearance from the trocar position. Otherwise, a user may manually input the insertion start position (the three-dimensional coordinates) with respect to the trocar position. In this case, it is determined whether or not the insertion start position designated by a user is included within the permissible range having the insertion direction corresponding to the trocar position, as a standard, and when the designated insertion start position is out of the permissible range, a user may be urged to reset the insertion start position.

In Step S604, the posture alignment processing section 412 calculates a direction of a vector passing through the trocar position (xt, yt, and zt) and the insertion start position (xs, ys, and zs) as the rotary angle (Rxs, Rys, and Rzs) for the axes x, y, and z, for example. The direction of a vector may be expressed through other methods in which the direction can be expressed as a posture. Then, the posture alignment processing section 412 determines the position and the posture of the forceps 22 (xs, ys, zs, Rxs, Rys, and Rzs) in which the direction of the vector and the major axis direction of the forceps 22 are combined, as the insertion posture. In Step S605, the posture alignment processing section 412 moves the slave arm 21 to the insertion posture, which has been determined in Step S604. As the movement is completed, the processing proceeds to Step S641, and a user is notified of the completion of the posture alignment with respect to the insertion posture via the GUI.

When the insertion start position retention section 422 retains not only the insertion start position (xs, ys, and zs) but also the insertion start position and the posture (xs, ys, zs, Rxs, Rys, and Rzs) including the posture, guidance may be directly performed to the insertion start position and the posture (xs, ys, zs, Rxs, Rys, and Rzs) through the articulation synchronous operation or the linear interpolation operation. In this case, for example, processing of Step S604 can be omitted.

Figure 9A:
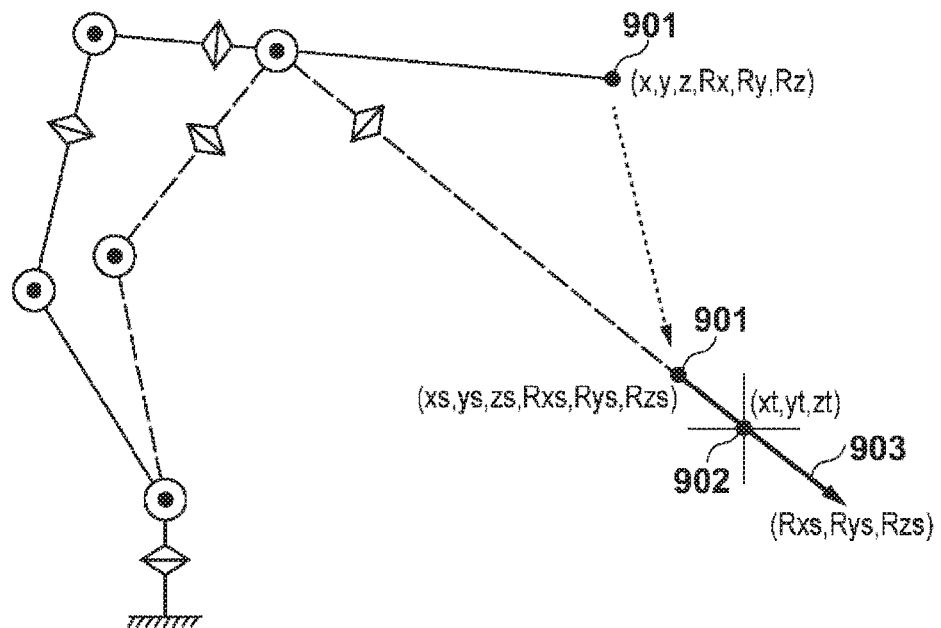
FIGS. 9A and 9B are diagrams illustrating the posture alignment operation of the slave arm in accordance with an exemplary embodiment.

FIG. 9A illustrates a state of the posture alignment operation performed in the automatic mode in accordance with an exemplary embodiment. A distal end portion 901 of the forceps 22 in arbitrary position and posture (x, y, z, Rx, Ry, and Rz) move to the insertion posture (xs, ys, zs, Rxs, Rys, and Rzs) through synchronous operations of each of the axes. In the insertion posture, the major axis of the forceps 22 coincides with a vector 903 in a direction in which the distal end portion 901 of the forceps 22 and a trocar position 902 are connected to each other.

Note that, there may be additionally provided a function for determining whether an operation thereafter can be safely conducted when the insertion posture (xs, ys, zs, Rxs, Rys, and Rzs) is derived. For example, it is calculated whether or not the insertion posture (xs, ys, zs, Rxs, Rys, and Rzs) is the position and the posture which a slave robot can take (whether or not the insertion posture is within an operational range of each articulation, or whether or not the insertion posture deviates from the operational range in the middle of the operation), whether or not the trocar (a patient) and the forceps interfere with each other or are too close to each other, whether or not the forceps can be inserted after the posture alignment operation (whether or not the insertion posture is within an operational range of each articulation, or whether or not the insertion posture deviates from the operational range in the middle of the operation), or the like. Then, as a result of the calculation, when it is determined that the operation thereafter cannot be safely conducted, a notice or a warning may be indicated for a user.

Figure 9B:
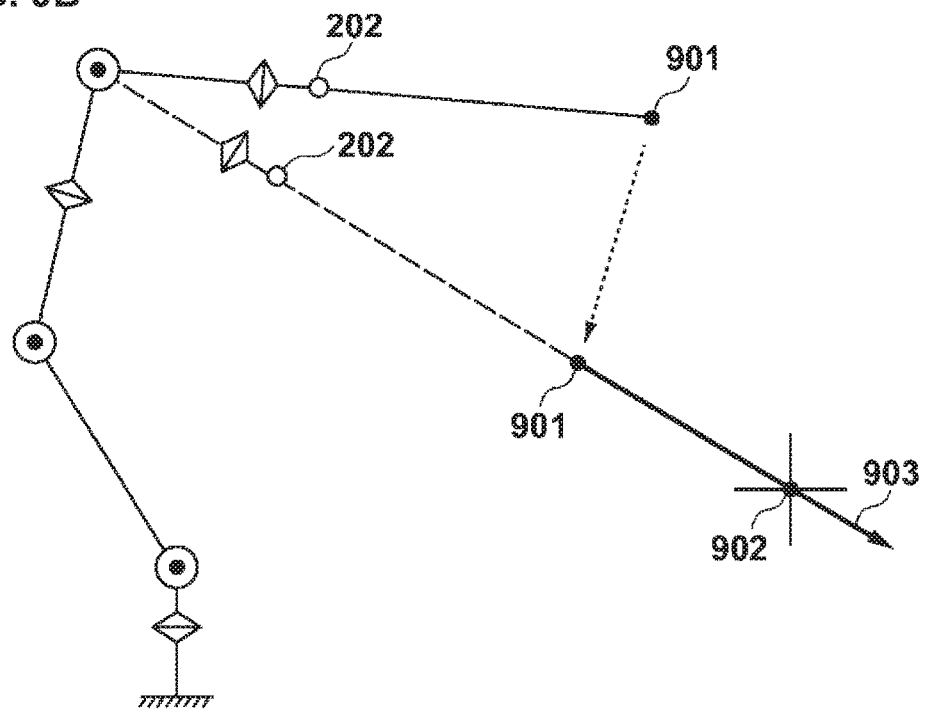

Meanwhile, in a case of other than the automatic mode, the processing proceeds from Step S602 to Step S606. In Step S606, the posture alignment processing section 412 fixes the first axis to the third axis (servo lock). Subsequently, in Step S607, the posture alignment processing section 412 calculates target positions (angles) of the fourth axis and the fifth axis. While causing current rotary angles of the first axis to the third axis to be immovable, the target positions (the angles) of the fourth axis and the fifth axis are calculated so as to cause the major axis of the forceps 22 to coincide with the direction of the vector, which connects the position of the forceps mounting portion 202 and the trocar position. For example, as illustrated in FIG. 9B, rotation amounts (the rotary positions) of the fourth axis and the fifth axis for moving the forceps mounting portion 202 so as to cause positions, such as a position of the forceps mounting portion 202, a position of the distal end portion 901, and a position of the trocar position 902 to be on a straight line are calculated.

In Step S608, the posture alignment processing section 412 determines which among the articulation synchronous operation mode, the jog operation mode, and the manual mode is the mode of the posture alignment processing. In a case of the articulation synchronous operation mode, the processing proceeds to Step S611. In Step S611, the posture alignment processing section 412 drives the fourth axis and the fifth axis of the slave arm 21 and moves the forceps mounting portion 202 (the distal end portion 901 of the forceps 22) to the target position which has been calculated in Step S607, through the articulation synchronous operation. When the movement to the target position ends, in Step S612, the posture alignment processing section 412 fixes the fourth axis and the fifth axis (servo lock), and notifies a user of the completion of the posture alignment in Step S641 via the GUI. In this manner, as illustrated in FIG. 9B, as the posture alignment processing drives the fourth axis and the fifth axis, the slave arm 21 moves to the insertion posture in which the vector 903 in the direction in which the distal end portion 901 of the forceps mounting portion 202 and the trocar position 902 are connected to each other coincides with the major axis direction of the forceps 22.

When the mode is the jog operation mode, the processing proceeds from Step S608 to Step S621. In Step S621, the posture alignment processing section 412 performs the jog operation for the fourth axis and the fifth axis in accordance with an input for operating the teaching pendant 12. In this case, the posture alignment processing can be efficiently executed by prohibiting the jog operation in a direction of being away from the target position, which has been calculated in Step S607. In Step S622, when there is an axis which has reached the target position, the posture alignment processing section 412 fixes the axis (servo lock). The jog operation is prohibited for the fixed axis. In Step S623, the posture alignment processing section 412 determines whether or not both the fourth axis and the fifth axis have been fixed to the target position. The processing returns to Step S621 unless at least one of the axes has reached the target position. If both the axes have reached and been fixed to the target position, the processing proceeds to Step S641, and the posture alignment processing section 412 notifies a user of the completion of the posture alignment via the GUI. The state of the operation of the slave arm 21 at the moment is as described above and as shown in FIG. 9B.

When the mode is the manual mode, the processing proceeds from Step S608 to Step S631. In Step S631, the posture alignment processing section 412 controls the fourth axis and the fifth axis so as to be able to be moved by an external force which a manipulator applies manually. In this case, the posture alignment processing can be efficiently executed by controlling the servo motor so as not to be manually moved in a direction of being away from the target position. In Step S632, when there is an axis which has reached the target position, the posture alignment processing section 412 fixes the axis (servo lock). Accordingly, the manual operation cannot be performed with respect to the fixed axis. In Step S633, the posture alignment processing section 412 determines whether or not both the fourth axis and the fifth axis have been fixed to the target position. The processing returns to Step S631 unless at least one of the axes has reached the target position. If both the axes have reached and been fixed to the target position, the processing proceeds to Step S641, and the completion of the posture alignment is notified to a user via the GUI. The state of the operation of the slave arm 21 at the moment is as described above and illustrated in FIG. 9A.

Note that, in Step S641, it is determined whether or not the direction of the forceps 22 of which the posture alignment has been completed is within the permissible range having the insertion direction which has been retained in the trocar position retention section 421 while being corresponding to the trocar position, as a standard, and when the direction is out of the permissible range, a warning to the effect thereof is issued. In this case, together with a warning to the effect of being out of the permissible range, for example, a user may be urged to execute the posture alignment in the automatic mode. In addition, it may be determined whether or not the direction of the forceps 22 after the posture alignment has been performed is within the above-described permissible range at the time when the target position is calculated in Step S607 described above. In this case, if the insertion direction is out of the permissible range, a warning can be issued to the effect thereof and the operation can be prohibited from being executed in the articulation synchronous operation mode, the jog operation mode, and the manual mode.

Returning to FIG. 5, when the posture alignment performed by the posture alignment processing section 412 is completed, the processing proceeds to Step S503. In Step S503, when an instruction is given through the GUI so as to insert the forceps 22 (instruction of insertion), the insertion evulsion processing section 413 drives the slave arm 21 so as to cause the forceps 22 to move in a parallel manner along the major axis direction thereof, and inserts the forceps 22 into an abdominal cavity of a patient from the trocar position.

Figure 7:
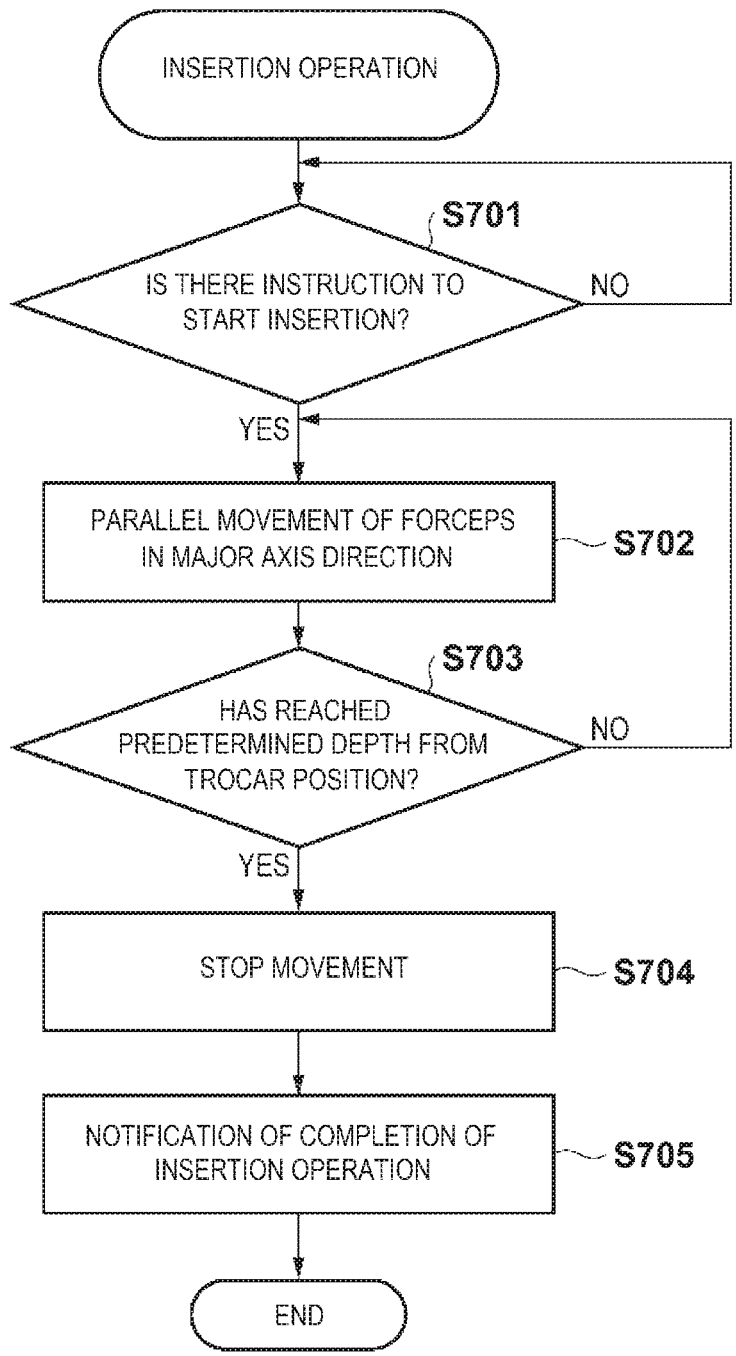
FIG. 7 is a flow chart illustrating an insertion operation in accordance with an exemplary embodiment.

FIG. 7 is a flow chart illustrating an insertion operation of the forceps 22. When an instruction of insertion is received through the GUI in Step S701, the insertion evulsion processing section 413 controls driving of each of the axes of the slave arm 21 so as to cause the forceps 22 to move along the major axis direction (the direction of the vector 903 in FIG. 9) of the forceps 22 in Step S702. Since the posture alignment of the forceps 22 has been completed by the posture alignment processing section 412 as described above, the forceps 22 advances toward the trocar position on account of a parallel movement performed in Step S702. Note that, a safer system can be established by suitably determining whether or not the forceps 22 advances toward the trocar position. For example, the determination can be realized by calculating misalignment (a distance) between a direction of the forceps shaft and the trocar position. Since the direction of the forceps shaft can be obtained as an equation of a straight line and the trocar position can be obtained as a coordinate value, a distance between a straight line and a point (a vertical distance: a shortest distance) may be obtained so as to determine that the forceps 22 is headed for the trocar position when the distance is zero (or less than a predetermined distance).

When the distal end portion of the forceps 22 passes through the trocar position and advances to a predetermined depth, the processing proceeds from Step S703 to Step S704, and the insertion evulsion processing section 413 stops the operation of the slave arm 21. Then, in Step S705, the insertion evulsion processing section 413 notifies a user of the completion of the insertion operation via the GUI. Otherwise, when the distal end of the forceps 22 passes through the trocar position and advances to a predetermined depth, the insertion evulsion processing section 413 may be in a standby state until a user determines the completion of the insertion operation. In this case, a user inputs confirmation of completion of the insertion operation via the GUI, thereby completing the insertion operation. It may be caused to suspend insertion and to allow evulsion until a user inputs the confirmation of completion.

Since the length of a tube portion of the trocar is equal to or less than approximately 100 mm in general, in consideration of the regions of the tube portion inside an abdominal cavity and the tube portion outside the abdominal cavity, a state of being inserted to the depth of, for example, approximately 50 mm may be considered to be the state of being inserted to a predetermined depth. In accordance with an exemplary embodiment, for example, an insertion amount may be set to, for example, approximately 10 mm. In consideration that the length of the forceps shaft ranges, for example, from approximately 300 mm to 400 mm, a state of being inserted to the depth ranging, for example, from approximately 30 mm to 40 mm may be set as the state of being inserted to a predetermined depth. After the completion of insertion, a trocar restriction operation can be performed (shifted to a state having a restriction operation), that is, the forceps 22 is operated while maintaining a state of passing through the trocar position.

Returning to FIG. 5, as the insertion operation has completed, the processing proceeds from Step S504 to Step S505. In Step S505, the restriction operation processing section 414 causes the slave arm 21 to follow the operation of the master arm 31 while the trocar is under restriction based on the three-dimensional position from the coordinate output device 32 and the in-operation signal from the foot switch 33. When the trocar is under restriction, the slave arm 21 is controlled so as to move the distal end portion of the forceps 22 to the three-dimensional position which is designated by the master arm 31 while the forceps 22 maintains the state of passing through the trocar position. In addition, an operation of following the operation of the master arm 31 can only be executed while the in-operation signal from the foot switch 33 is in an ON state.

Figure 8:
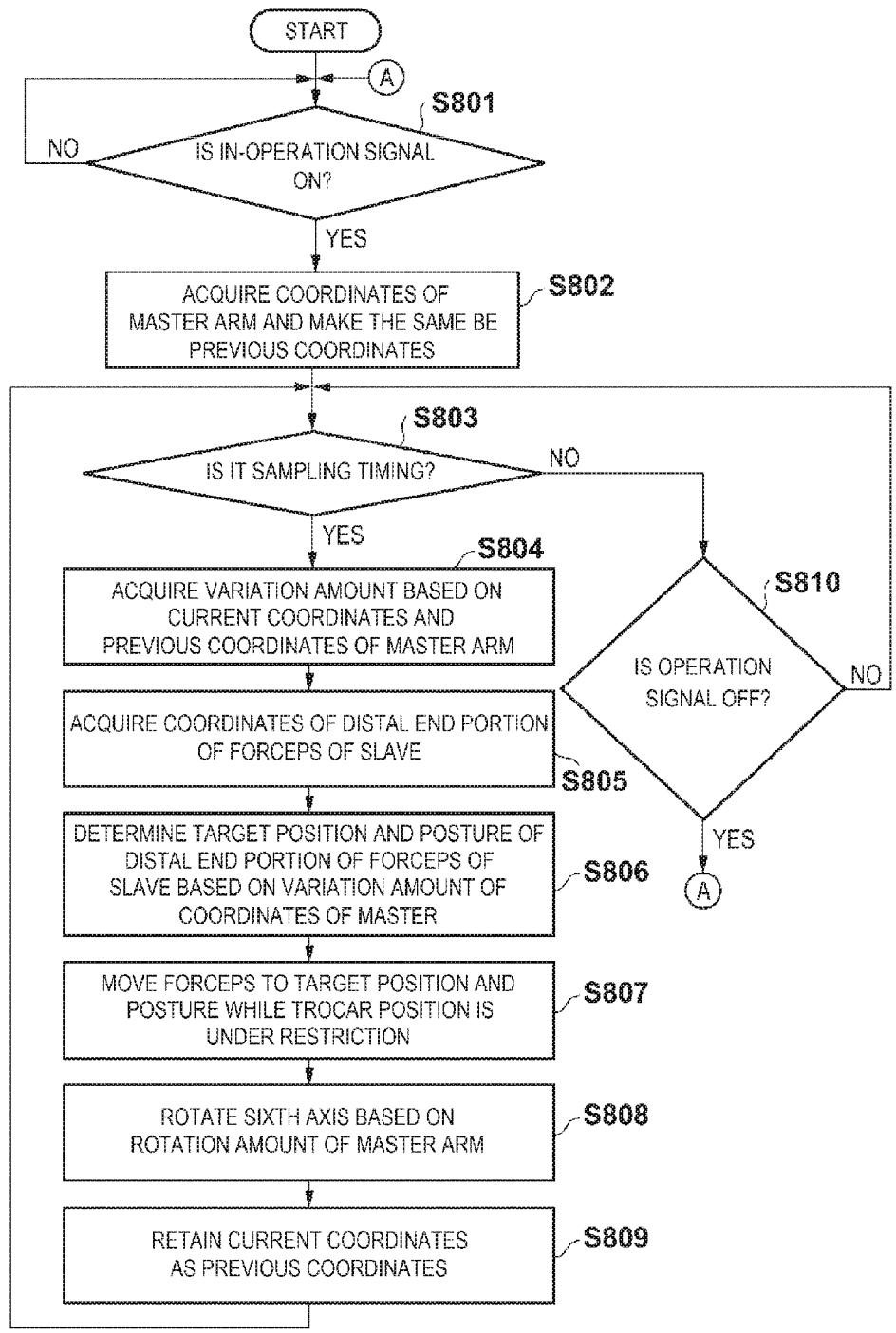
FIG. 8 is a flow chart illustrating driving processing of the slave arm while a trocar is under restriction in accordance with an exemplary embodiment.

Descriptions will be given regarding processing of an operation while the trocar is under restriction with reference to the flow chart in FIG. 8. In Step S801, the restriction operation processing section 414 determines whether or not the in-operation signal from the foot switch 33 is ON. When the in-operation signal is ON, the processing proceeds to Step S802. The coordinate processing section 415 acquires the coordinate value from the coordinate output device 32, and the acquired value is referred to as previous coordinates (initial coordinates). Note that, the coordinate values acquired from the coordinate output device 32 herein are the position (x, y, and z) corresponding to the three-dimensional position of the distal end portion 305 of the master forceps shaft 302, and the rotary angle (r) of the master forceps shaft 302. When a predetermined sample interval elapses after the previous coordinates have been acquired and sample timing is obtained, the processing proceeds from Step S803 to Step S804.

Figure 10:
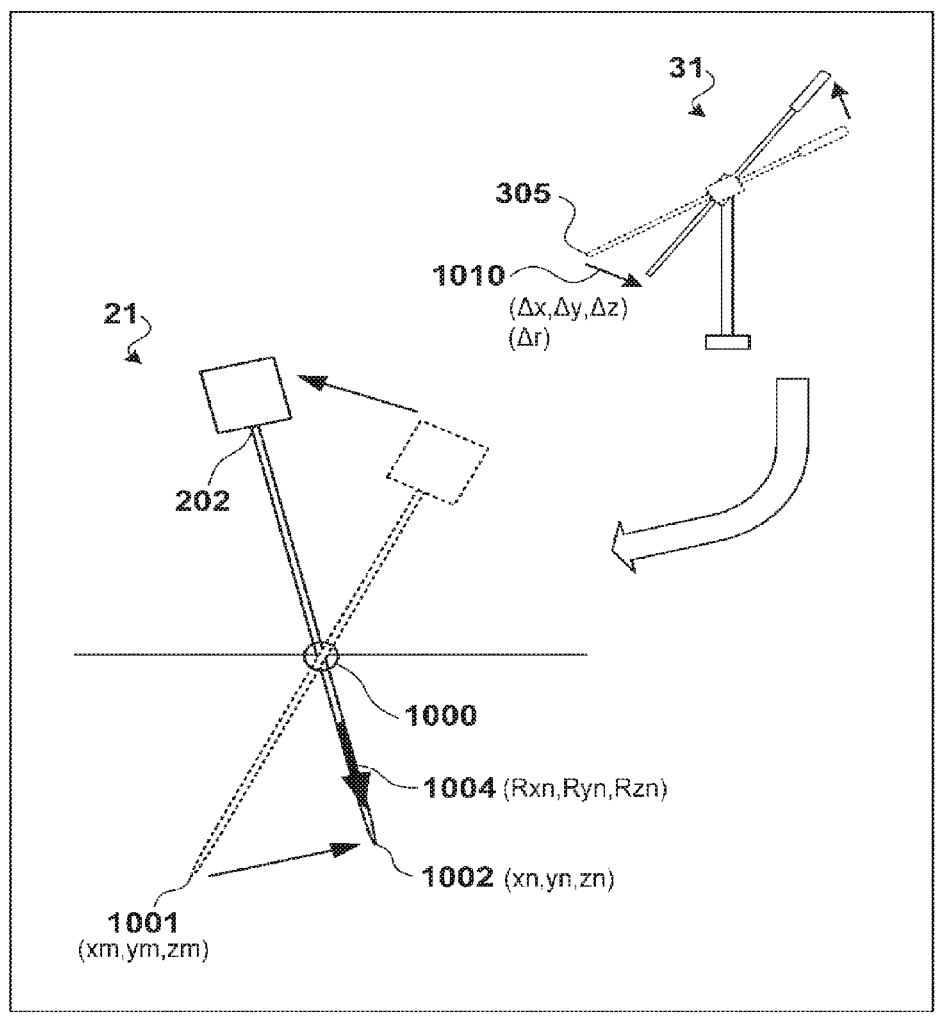
FIG. 10 is a diagram illustrating operations of the master arm and the slave arm while the trocar is under restriction.

In Step S804, the coordinate processing section 415 acquires the coordinate value from the coordinate output device 32 as current coordinates. Then, the coordinate processing section 415 calculates a difference between the previous coordinates and the current coordinates, and obtains a movement amount (Δx, Δy, and Δz) of the distal end portion 305 of the master forceps shaft 302 and the rotation amount (Δr) of the master forceps shaft 302 in the sample interval. Then, the movement amount and the rotation amount are output to the restriction operation processing section 414, which state is illustrated in FIG. 10. The coordinate processing section 415 calculates a movement amount 100 ((Δx, Δy, and Δz) and (Δr)) of the distal end portion 305 caused by an operation of the master arm 31.

Subsequently, in Step S805, the restriction operation processing section 414 acquires the three-dimensional coordinates (xm, ym, and zm) of a current distal end portion position 1001 of the forceps 22 mounted in the slave arm 21, based on the rotary position (θ1 to θ5) of the first axis to the fifth axis and the length (forceps coordinates) of the forceps 22. Then, in Step S806, the restriction operation processing section 414 calculates the three-dimensional coordinates (xn, yn, and zn) of a target distal end portion position 1002 based on the current distal end portion position 1001 (xm, ym, and zm), and the movement amount (Δx, Δy, and Δz) acquired from the coordinate processing section 415. Moreover, the restriction operation processing section 414 calculates a vector 1004 (Rxn, Ryn, and Rzn) in a direction in which the target three-dimensional coordinates (xn, yn, and zn) and a trocar position 1000 are connected to each other. In this manner, the target position and posture (xn, yn, zn, xn, Ryn, and Rzn) of the forceps 22 in accordance with the movement amount (Δx, Δy, and Δz) of the master arm 31 are determined. As described above, the spatial position at a destination of the distal end portion of the forceps 22 is determined in accordance with an operation amount (a variation amount) of the master arm 31 caused by a user's operation.

In Step S807, the restriction operation processing section 414 moves the forceps 22 to the target position and posture while maintaining a state where the forceps 22 passes the trocar position 1000, that is, while the trocar position is under restriction. Then, in Step S808, the restriction operation processing section 414 rotates the sixth axis in accordance with the rotation amount (Δr) of the master forceps shaft 302. In this manner, while the trocar position is under restriction, the forceps 22 moves to a position instructed by the master arm 31 and a rotative operation of the forceps shaft instructed by the master arm 31 is executed.

In accordance with an exemplary embodiment, for example, the processing of Step S808 can be executed simultaneously with that of Step S806. Accordingly, movement processing of the forceps 22 to the target position and posture can be executed more efficiently.

Note that, while the above-described trocar restriction operation is performed, it is desirable that calculation processing for the target position and posture of the forceps 22 is executed, and it can be desirable to check whether or not the forceps 22 have been inserted by a predetermined amount with respect to the trocar position (whether or not the forceps 22 have been inserted further than the minimum insertion amount), which can be because the movement of the forceps mounting portion 202 becomes fast and an operation of each of the axes of the slave arm becomes extremely fast when the distal end portion of the forceps is guided at a predetermined speed in a state where the insertion amount of the forceps is small. When an operation speed of each of the axes of the slave arm exceeds a predetermined speed, each of the articulations cannot follow a target value. As a result, there is a possibility that an operation in a state where the forceps shaft maintains the trocar position cannot be performed. Therefore, in order to help ensure a safe operation, there is a need to check whether the forceps have been inserted by a predetermined amount with respect to the trocar position.

Then, when the target value is generated in a direction of evulsion from a state where the forceps 22 have been inserted by a predetermined amount (the minimum insertion amount) with respect to the trocar position, processing for causing the target value to return to the previous target value (in a state where the forceps have been inserted by a predetermined amount with respect to the trocar position), or the like is performed. According to such processing, the forceps 22 can maintain a state of being inserted by equal to or greater than a predetermined amount with respect to the trocar position. In addition, it can be desirable that a manipulator is presented with a fact that the target value in the evulsion direction is generated from the state where the forceps have been inserted by a predetermined amount with respect to the trocar, in a method in any form. In order to attain the aforementioned condition, the manipulator can be presented with the fact by senses of force, hearing, or sight, for example.

Note that, during the insertion of the forceps described above, the aforementioned minimum insertion amount or an insertion amount greater than the minimum insertion amount is employed as a threshold value for the determination at the time of a shift from Step S703 to Step S704, and thus, it is possible to smoothly shift to the state of controlling while the trocar is under restriction.

In addition, similar to that described above, since the length of the tube portion of the trocar is equal to or less than, for example, approximately 100 mm, in consideration of the regions of the tube portion inside an abdominal cavity and the tube portion outside the abdominal cavity, the above-described minimum insertion amount may be set to, for example, approximately 50 mm. Naturally, if followability of the slave arm 21 can be sufficiently obtained, an insertion amount of, for example, approximately 10 mm may be set as the minimum insertion amount. In addition, in consideration that the length of the forceps shaft ranges, for example, approximately from 300 approximately mm to 400 mm, for example, approximately ten percent thereof, that is, for example, a range approximately from 30 mm to 40 mm may be set as the minimum insertion amount. In this case, the minimum insertion amount varies in accordance with the length of the mounted forceps.

Moreover, in accordance with an exemplary embodiment, the maximum insertion amount may be designated so as to avoid a collision between the forceps mounting portion of the robot (outside the forceps shaft portion) and the trocar, or to avoid unexpected contact or damage to the internal organs caused by inserting the forceps further than necessary. In consideration that the length of the forceps shaft ranges, for example, from approximately 300 mm to 400 mm, a state of being inserted to the depth ranging, for example, from approximately 250 mm to 300 mm can be set as the maximum insertion amount. Naturally, in order to help ensure the operation region, the maximum insertion amount needs to be equal to or greater than the above-described predetermined insertion amount (the minimum insertion amount). When the target value in a direction of being inserted further than the maximum insertion amount is generated from the state where the forceps have been inserted by a predetermined amount with respect to the trocar, processing for causing the target value to return to the previous target value (in a state where the forceps have been inserted by a predetermined amount with respect to the trocar), or the like can be performed. Thus, the state where the forceps have been inserted by a predetermined amount with respect to the trocar can be maintained. In addition, in accordance with an exemplary embodiment, it can be desirable that a manipulator is presented with a fact that the target value in the insertion direction exceeding the maximum insertion amount is generated from the state where the forceps have been inserted by a predetermined amount with respect to the trocar, in a method in any form. For example, the manipulator can be presented with the fact by senses of force, hearing, or sight.

In Step S809, the coordinate processing section 415 retains the current coordinates acquired in Step S804, as the previous coordinates. Then, the processing returns to Step S803, and the above-described processing is repeated. When the in-operation signal is in an OFF state while waiting for successive sample timing, the processing returns to Step S801 from Step S810. In this manner, only while the in-operation signal is in an ON state by the foot switch 33, the slave arm 21 follows movement of the distal end portion of the master arm 31. In the above-described the embodiment, algorithm for generating the target value is presented based on the relative movement amount of the previous coordinates with respect to the previous coordinates for each sampling. However, naturally, coordinates at certain timing may be set as a standard (the initial coordinates) instead of generating for each sampling. For example, the coordinates when the in-operation signal is ON may be set as the initial coordinates, and while the in-operation signal is ON, the target value may be generated based on the relative coordinates from the initial coordinates.

Returning to FIG. 5, when evulsion of the forceps 22 is instructed via the GUI, the processing proceeds from Step S506 to Step S507. In Step S507, the insertion evulsion processing section 413 draws the forceps 22 out of the patient's body along the major axis direction of the forceps 22 at the moment. When the distal end portion of the forceps 22 passes through the trocar position and is away from the trocar position by a predetermined distance, an evulsion operation is completed (Step S508), and the forceps 22 wait for an instruction for moving to a standby position (Step S509). At this moment, the trocar restriction operation is cancelled. When a standby instruction is input through the GUI, the slave arm 21 moves to a predetermined standby position which has been retained in the standby position retention section 423 (Step S509).

Here, in accordance with an exemplary embodiment, a function for determining whether the evulsion operation can be safely conducted may be added. For example, it is calculated whether or not the insertion posture is the position and the posture which the slave robot can take (whether or not the insertion posture is within an operational range of each articulation, whether or not the insertion posture deviates from the operational range in the middle of the operation), or the like with respect to the operation in which the distal end portion of the forceps 22 passes through the trocar position and is away from the trocar position by a predetermined distance, and when there is a possibility that the evulsion operation thereafter cannot be safely conducted, a notice or a warning may be clearly presented to a user.

Note that, as described above, the position and the posture of the forceps 22, and the trocar position at the time of completion of the evulsion operation in Step S507 may be retained as the insertion posture when the forceps insertion is performed in the automatic mode so as to be utilized in the above-described posture alignment (Step S502). In this manner, for example, in a case or the like where the forceps are reinserted from the same trocar position after replacement of the forceps which has been used, the trocar position, and the insertion start position and the posture can be simply selected, thereby being convenient. In addition, in this case, since the stored insertion posture is applied as it is, there is no need to calculate the insertion posture in Step S604.

Note that, there is a need to maintain a state where a shaft axis (hereinafter, referred to as the forceps shaft axis) of the forceps 22 passes through the trocar position with no error or with an error equal to or less than a tolerance value in the operation while the trocar of the slave arm 21 is under restriction. It is because there is a possibility that excessive force is generated on an abdominal wall of a patient, thereby causing an occurrence of an unfavorable state when the error is excessive. However, a state where the forceps shaft axis passes the trocar position with no error is not necessarily able to be maintained due to degradation of followability with respect to a target trajectory of the slave arm at the time of a high-speed operation or in a peculiar posture and the vicinity of a so-called robot. Therefore, there is a need to derive a distance between the trocar position and the forceps shaft axis (for example, a vertical distance) and to monitor that the distance is equal to or less than a predetermined amount. In addition, there is a need for a manipulator to be clearly indicated when the distance between the trocar position and the forceps shaft axis is in a state of being equal to or greater than a predetermined amount. Moreover, a safer system can be established by controlling the distance to avoid being equal to or less than a predetermined amount when the distance between the trocar position and the forceps shaft axis is equal to or greater than a predetermined amount, that is, by executing controlling such as slowing down the speed of the slave arm, stopping thereof, or the like in a forcible manner, for example.

In addition, the movement amount ($\Delta x$, $\Delta y$, and $\Delta z$) of the master arm 31 may be decreased or increased by the coordinate processing section 415 so as to be reflected to movement of the forceps 22. It is possible to prevent the hands from shaking by decreasing the movement amount, that is, by decreasing an operation (decreasing the movement amount of the distal end of the forceps 22 caused by the slave arm 21 with respect to the movement amount of the distal end portion 305 of the master forceps shaft 302).

In addition, information indicating a relationship between an imaging direction of the camera 41 and the position of the slave arm 21 may be input to the coordinate processing section 415 so that the coordinate processing section 415 converts the movement direction indicated by the movement amount of the master arm 31 based on the relationship which has been input. For example, the horizontal and vertical directions of an image in the monitor 43 can substantially coincide with the horizontal and vertical directions in operation of the master arm 31. In this manner, the movement direction of the forceps 22 which has been displayed in the monitor 43 can substantially coincide with the movement direction of the distal end portion of the master arm 31, thereby improving operation characteristics for an operator.

In addition, since the master arm 31 can be installed at an arbitrary position on account of a simple and compact structure, an operator can be freed from a situation in which surgery has to be conducted in an unstable posture due to positions of a surgical table, a patient, an assistant, and the like, thereby being able to perform operation in an optimal posture at all times.

In addition, in the embodiment described above, a coordinate system is not particularly described. However, if the factors x, y, and z in the world coordinate system are applied, it is advantageous when multiple slave arms are applied.

As described above, according to the embodiment described above, since a support system for laparoscopic surgery can be established by applying a so-called industrial robot, it is inexpensive and it is possible to obtain a system which is excellent in flexibility with respect to operation for an operator. For example, the trocar position can vary without changing the installation position of the arm when being within the operation region of the industrial robot (the slave arm). Therefore, it is possible to flexibly cope with multiple trocar positions with one slave arm.

In addition, in the embodiment described above, descriptions are given that the distal end of the forceps 22 is caused to match the spatial position instructed by the master arm 31. However, the embodiment is not limited thereto, and there is no need to mention that a predetermined portion of the forceps 22 may be caused to match. For example, when the gripper is provided at the distal end portion of the forceps 22 and the gripper is configured to be rotatable around two rotary axes such as the roll axis and the yaw axis, the rotary portion of the gripper may be the portion to be caused to match the spatial position instructed by the master arm 31.

Note that, in the embodiment described above, the end effector has been described as the forceps. However, the embodiment is not limited thereto, as described above. For example, the end effector may be an endoscope (the laparoscope and the thoracoscope) and other surgical instruments (an energy device and a treatment tool). In addition, in the embodiment described above, descriptions are given regarding an example in which a medical manipulator is applied to surgery for the inside of an abdominal cavity. However, there is no need to mention that the embodiment can be applied to surgery for a thoracoabdominal cavity, the inside of the skull, the inside of the heart, or the like. In accordance with an exemplary embodiment, for example, any site may be subjected thereto as long as the surgery is the minimally invasive surgery, which can be conducted by inserting a medical instrument into a human body through a smaller insertion port and gives fewer burdens to the human body.

The detailed description above describes a medical manipulator and a method of controlling the same in a remote operation-type surgery system. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A medical manipulator comprising:
  a multiple-degree freedom slave arm, which can be mounted with a medical instrument;
  a master arm configured that an operator instructs the multiple-degree freedom slave arm to make a movement of the medical instrument;
  a memory configured to retain an insertion port position indicating a spatial position of an insertion port for inserting the medical instrument mounted in the multiple-degree freedom slave arm into a human body;
  a touch panel display configured to receive an instruction by the operator; and
  a controller configured to control the multiple-degree freedom slave arm so as to perform a predetermined operation related to inserting the medical instrument into the human body from the insertion port position based on the instruction of the operator via the touch panel display; and
  wherein the controller is configured to control the multiple-degree freedom slave arm so as to move a distal end portion of the medical instrument to spatial coordinates instructed by the operator via the master arm while maintaining a state where the medical instrument passes through the insertion port position.

2. The medical manipulator according to claim 1,
  wherein the medical instrument includes a shaft portion which is inserted into the human body,
  wherein the memory is configured to retain an insertion direction corresponding to the insertion port position, and
  wherein the controller performs the predetermined operation including moving the medical instrument in a parallel manner in a direction within a permissible range having the insertion direction as a standard to the spatial position of the insertion port along a shaft axis direction based on the instruction of the operator via the touch panel display.

3. The medical manipulator according to claim 1, further comprising:
  wherein the controller is configured to:
    remove the medical instrument from an inside of the human body while causing the medical instrument to pass through the insertion port position and cancel the movement of the medical instrument instructed by the master arm after an entirety of the medical instrument is removed from the insertion port position.

4. The medical manipulator according to claim 3,
  wherein the controller is configured to cancel the movement of the medical instrument instructed by the master arm after the entirety of the medical instrument is extracted from the insertion port position and moves further in a direction of the removal by a predetermined amount thereafter.

5. The medical manipulator according to claim 3,
  wherein the controller is configured to move the multiple-degree freedom slave arm in a predetermined standby state after removal of the medical instrument is completed and the movement of the medical instrument instructed by the master arm is cancelled.

6. The medical manipulator according to claim 1,
  wherein the controller is configured to maintain a state where the medical instrument is inserted equal to or greater than a minimum insertion amount with respect to the insertion port under the movement of the medical instrument instructed by the master arm.

7. The medical manipulator according to claim 1,
  wherein the controller is configured to maintain a state where an insertion amount of the medical instrument with respect to the insertion port position does not exceed a maximum insertion amount under the movement of the medical instrument instructed by the master arm.

8. The medical manipulator according to claim 6,
  wherein the controller is configured to shift controlling of the multiple-degree freedom slave arm to a state of being driven under the movement of the medical instrument instructed by the master arm as the insertion amount of the medical instrument from the insertion port position becomes equal to or greater than the minimum insertion amount.

9. A method of controlling a medical manipulator including a multiple-degree freedom slave arm, which can be mounted with a medical instrument, a master arm configured that an operator instructs the multiple-degree freedom slave arm to make a movement of the medical instrument and a touch panel display configured to receive an instruction by the operator, the method comprising:
  retaining an insertion port position indicating a spatial position of an insertion port for inserting the medical instrument mounted in the multiple-degree freedom slave arm into a human body, in a memory;
  controlling the multiple-degree freedom slave arm so as to perform a predetermined operation of the multiple-degree freedom slave arm related to inserting the medical instrument into the human body from the insertion port position based on the instruction of the operator via the touch panel display; and
  driving the multiple-degree freedom slave arm so as to move a distal end portion of the medical instrument to spatial coordinates instructed by the operator via the master arm while maintaining a state where the medical instrument passes through the insertion port position.

10. The method according to claim 9, wherein the medical instrument includes a shaft portion, and comprising:
  retaining an insertion direction corresponding to the insertion port position in the memory, and
  controlling the multiple-degree freedom slave arm to move the medical instrument in a parallel manner in a direction within a permissible range having the insertion direction as a standard to the spatial position of the insertion port along a shaft axis direction based on the instruction of the operator via the touch panel display.

11. The method according to claim 9, comprising:
  removing the medical instrument from an inside of the human body while causing the medical instrument to pass through the insertion port position; and canceling the movement of the medical instrument instructed by the master arm after the entirety of the medical instrument is removed from the insertion port position.

12. The method according to claim 11, comprising:

canceling the movement of the medical instrument instructed by the master arm after the entirety of the medical instrument is removed from the insertion port position and moves further in a direction by a predetermined amount.

13. The method according to claim 11, comprising:

moving the multiple-degree freedom slave arm to be in a predetermined standby state after removal of the medical instrument is completed and the movement of the medical instrument instructed by the master arm is cancelled.

14. The method according to claim 11, comprising:

maintaining a state where the medical instrument is inserted equal to or greater than a minimum insertion amount with respect to the insertion port under the movement of the medical instrument instructed by the master arm.

15. The method according to claim 11, comprising:

maintaining a state where an insertion amount of the medical instrument with respect to the insertion port position does not exceed a maximum insertion amount under the movement of the medical instrument instructed by the master arm.

16. The method according to claim 14, comprising:

controlling of the multiple-degree freedom slave arm to a state of being driven under the movement of the medical instrument instructed by the master arm as the insertion amount of the medical instrument from the insertion port position becomes equal to or greater than the minimum insertion amount.

17. The medical manipulator according to claim 1, wherein the predetermined operation includes a posture alignment operation in which a position of the medical instrument is placed toward the insertion port position and a posture of the medical instrument is aligned toward the insertion port position based on the instruction of the operator via the touch panel display.

18. The medical manipulator according to claim 1, wherein the predetermined operation is performed before associating the master arm and the multiple-degree freedom slave arm, and the movement of the medical instrument instructed by the master arm is performed after associating the master arm and the multiple-degree freedom slave arm.

19. The method according to claim 9, wherein the predetermined operation includes a posture alignment operation in which a position of the medical instrument is placed toward the insertion port position and a posture of the medical instrument is aligned toward the insertion port position based on the instruction of the operator via the touch panel display.

20. The method according to claim 9, wherein the predetermined operation is performed before associating the master arm and the multiple-degree freedom slave arm, and the movement of the medical instrument instructed by the master arm is performed after associating the master arm and the multiple-degree freedom slave arm.

* * * * *